(12) United States Patent
Lee et al.

(10) Patent No.: US 9,814,549 B2
(45) Date of Patent: Nov. 14, 2017

(54) METHOD FOR CREATING FLEXIBLE ARCH MODEL OF TEETH FOR USE IN RESTORATIVE DENTISTRY

(71) Applicant: Dentsply International, Inc., York, PA (US)

(72) Inventors: Jinho Lee, Belmont, MA (US); Alexander Yarmarkovich, Swampscott, PA (US); Kenneth Michael Flowers, Lexington, MA (US)

(73) Assignee: DENTSPLY SIRONA, INC., York, PA (US)

( * ) Notice: Subject to any disclaimer, the term of this patent is extended or adjusted under 35 U.S.C. 154(b) by 152 days.

(21) Appl. No.: 14/853,284

(22) Filed: Sep. 14, 2015

(65) Prior Publication Data

US 2017/0071706 A1    Mar. 16, 2017

(51) Int. Cl.
*A61C 13/00* (2006.01)
*A61C 13/34* (2006.01)

(52) U.S. Cl.
CPC .......... *A61C 13/0004* (2013.01); *A61C 13/34* (2013.01)

(58) Field of Classification Search
CPC ....... A61C 7/002; A61C 9/004; A61C 9/0046; A61C 9/0053; A61C 13/0004; A61C 13/34; G06T 2207/30036
USPC ......................................... 433/167, 213, 215
See application file for complete search history.

(56) References Cited

U.S. PATENT DOCUMENTS

| | | | |
|---|---|---|---|
| 7,551,760 B2 * | 6/2009 | Scharlack | A61C 13/0004 382/128 |
| 8,727,776 B2 | 5/2014 | Mehl | |
| 2006/0063135 A1 | 3/2006 | Mehl | |
| 2007/0154868 A1 | 7/2007 | Scharlack et al. | |
| 2009/0246726 A1 | 10/2009 | Chelnokov et al. | |
| 2010/0151404 A1 | 6/2010 | Wu et al. | |
| 2011/0110575 A1 | 5/2011 | Banumathi et al. | |

(Continued)

OTHER PUBLICATIONS

U.S. Appl. No. 14/609,774, Jan. 30, 2015, Lee et al.

(Continued)

*Primary Examiner* — Nicholas Lucchesi
(74) *Attorney, Agent, or Firm* — Douglas J. Hura; David A. Zdurne; Leana Levin

(57) ABSTRACT

A flexible arch model (FAM) is computed to capture and parameterize the variations of the multiple real dental arches in a training set to reconstruct missing teeth in a patient's dental anatomy. Building the FAM includes acquiring multiple sets of digitized dental arches with a pair of maxillary (upper) and mandibular (lower) jaws in the right relative position and gathering a pre-defined set of landmark points on the occlusal surface of each arch all in the same order and same corresponding positions across multiple samples. The gathered vectors of landmark points are used to perform statistical modeling (e.g. Principal Component Analysis) to create a linear subspace of the feature points with the basis of principal components (when PCA is used) found during the procedure. An arbitrary set of landmark points on a pair of upper and lower arches can be reconstructed by a linear combination of the principal components within a reasonable range of variations captured from the training samples. The reconstructed landmark points can be used to build a full set tooth model in a dental arch.

20 Claims, 4 Drawing Sheets

(56) References Cited

U.S. PATENT DOCUMENTS

| | | |
|---|---|---|
| 2011/0212419 A1 | 9/2011 | Schweiger |
| 2012/0171642 A1 | 7/2012 | Mehl |
| 2013/0095448 A1 | 4/2013 | Phan et al. |
| 2014/0229145 A1 | 8/2014 | Van Lierde |
| 2014/0379356 A1 | 12/2014 | Sachdeva et al. |
| 2016/0004811 A1* | 1/2016 | Somasundaram ...... G06F 17/50 703/11 |
| 2016/0220173 A1* | 8/2016 | Ribnick ............... A61B 5/4557 |

OTHER PUBLICATIONS

Allen et al., "The Space of Human Body Shapes: Reconstruction and Parameterization from Range Scans", Proceedings of Siggraph, Jul. 2003, 587-594.

Blanz et al., "A Morphable Model for the Synthesis of 3d Faces", In Proceedings of Siggraph Aug. 1999, 99, 187-194.

Fletcher et al., "Statistics of Shape Via Principal Geodesic Analysis on Lie Groups", In Proceedings of Computer Vision and Pattern Recognition (CVPR), Jun. 2003, 95-101.

Jones et al., "Multidimensional Morphable Models: A Framework for Representing and Matching Object Classes", International Journal of Computer Vision, 1998, 29(2), 107-131.

Kanai et al., "Three Dimensional Geometric Metamorphosis Based on Harmonic Maps", The Visual Computer, 1998, 14, 166-176.

Kanungo et al., "An Efficient K-Means Clustering Algorithm: Analysis and Implementation", IEEE Trans. Pattern Analysis and Machine Intelligence, American University, Washington DC, Jul. 7, 2002, 24(7), 36 pages.

Kry et al., "Eigenskin: Real Time Large Deformation Character Skinning in Hardware", In Proceedings of Siggraph, Jul. 2002, 153-159.

Lemke et al., "Generating Geometrically Deformable Models by Statistical Shape Modeling for Computer Aided Dental Restorations", CARS, 2000, 841-845.

Lorenz et al., "Generation of Point Based 3d Statistical Shape Models for Anatomical Objects", Computer Vision and Image Understanding, Feb. 2000, 77(2), 175-191.

MacQueen, "Some Methods for Classification and Analysis of Multivariate Observations", Proceedings of the $5^{th}$ Berkeley Symposium on Mathematical Statics and Probability, University of California, Los Angeles, 1967, 281-297.

Pighin et al., "Synthesizing Realistic Facial Expressions from Photographs", Proceedings of SIGGRAPH, 2006, 10 pages.

Pokhariyal et al., "Simulation Model for Dental Arch Shapes", East Afr Med J., Nov. 2004, 81(11), 599-602.

Rijal et al., "Shape Model of the Maxillary Dental Arch Using Fourier Descriptors With an Application in the Rehabilitation for Edentulous Patient", Conf Proc IEEE Eng Med Biol Soc., 2013, 209-212.

Shen et al. "Hippocampal Shape Analysis: Surface-Based Representation and Classification", Proc. Spie 5032, Medical Imaging, Image Processing, May 16, 2003, 253, 1-12.

Zheng et al., "A Novel 3d Morphing Approach for Tooth Occlusal Surface Reconstruction", Computer Aided Design, Mar. 2011, 43(3), 293-302.

\* cited by examiner

METHOD FOR CREATING FLEXIBLE ARCH MODEL OF TEETH FOR USE IN RESTORATIVE DENTISTRY

TECHNICAL FIELD

The invention relates to techniques for creating flexible arch models of teeth for use in restorative dentistry and, more particularly, to a method for automated creation of flexible arch models of teeth for use in digital restorative design.

BACKGROUND

In restorative dentistry, tooth shapes are typically generated based on a small set of sample tooth shapes called library teeth. Such library teeth are stored in tooth libraries and manipulated using 3D digital editing techniques that are equivalent to the physical processes of sculpting in wax and clay (i.e., by adding or removing material digitally from areas on the surface of the model in a manner analogous to adding or removing wax in physical modeling). This allows for a wide variation, but provides no means for assuring that the result continues to be a natural tooth shape. Techniques for making the tooth models using statistical techniques have been described by the present inventors in U.S. patent application Ser. No. 14/609,774, filed Jan. 30, 2015, the contents of which are incorporated herein by reference. However, to the inventors' knowledge, such statistical techniques have not been applied to the creation of bridges and arch models encompassing multiple teeth. As will be appreciated by those skilled in the art, bridges and arches are significantly more complicated than crowns as there are additional anatomical constraints amongst the respective teeth in the arch model.

Advances in digital dentistry have made available a lot of software tools in restorative dentistry for performing functions from implant planning to crown design. Although these software tools facilitate complicated dental process with higher precision, manipulating these tools often still requires skilled dental professionals to perform certain operations in a specific way within the range a tool allows. For example, it is hard to find a software tool that is able to create a complete crown restoration for a sequence of two or more missing teeth in a fully automatic manner. Two of the fundamental technical challenges that make such automatic generation of restoration very difficult are obtaining dentition information of a scanned (digitized) dental arch and enforcing anatomical constraints between the consecutive restorative units using an automatic computerized process.

Partially addressing these problems, in earlier work the inventors developed an algorithm to build an anatomical crown model called ACM based on a statistical analysis of many real tooth samples of each tooth type. ACM has been proven to be an effective morphable crown model that can be used in both interactive crown design and automated crown initialization. However, there is a lack of proper support in the model to represent the relationship of two or more consecutive tooth units in a dental arch. Methods are needed for better addressing the challenges presented when modeling the relationship of two or more consecutive tooth units in a dental arch. The invention addresses these and other needs in the art.

SUMMARY

The methods described herein address the two main technical challenges of obtaining dentition information of a scanned (digitized) dental arch and enforcing anatomical constraints between the consecutive restorative units and hence pave the way for furthering the level of automation in digital restorative dentistry. The methods described herein provide a full dental arch model available for use toward digital restoration design. Existing software tools treat each crown model separately and do not allow two or more crown units to vary together and to be constrained in an anatomically correct relationship between each other or in the context of the whole dental arch. The arch model described herein addresses these issues by implementing a Flexible Arch Model (FAM) that incorporates a correct anatomical relationship of two or more restorative units based on a statistical analysis of many digitized dental arches.

FAM addresses the problems of the prior art by creating a full arch model comprising the upper and lower jaw in a correct relative position. The upper and lower jaw in the arch model includes a set of complete 3D geometry of individual tooth models. The arch model is as flexible as possible to change its overall shape (width, size, curve of Wilson, curve of Spee, etc.) within a reasonable range based on a small set of parameters. An algorithm has also been developed to fit the constructed arch model to an arbitrary digitized scan of the upper and lower arch of a patient's mouth whether the scan consists of a complete set of teeth or a partial set of teeth. This fitting process is about finding an optimal set of arch parameters and transform parameters that provide the closest match to the target arch scan.

An analytical model (including a non-uniform rational basis spline or NURBS) may be used to represent a dental arch with a small number of parameters such as overall width, height, depth (i.e. bounding box) and curvatures on an important area. Such an approach is desirable because it would be more intuitive to control the arch shape based on those parameters instead of performing a statistical analysis. However, the inventors use principal component analysis (PCA) in an exemplary embodiment of a statistic model suitable to build a new arch model because it is difficult to constrain the shape of the arch to be within an anatomical (realistic) shape based on the range of analytical parameters. Those constraints are embedded in a statistical model inherently. Also, the inventors recognized that there is a need for more than a 3D curve for the arch model that can be used for a variety of applications more effectively. For example, the model should be able to represent location and size of each tooth in the arch, the alignment of cusps, and occlusal surface that would reflect dental anatomical features such as the curve of Spee and the curve of Wilson.

The inventors have recognized in their prior work with ACMs that an individual crown can be constrained to be within the subspace of tooth shape built by k-means clustering. A similar constraint can be established if a statistical method is performed on many samples of real dental arches. This is a natural extension of ACM to represent a full dental arch using ACM as a building block. The inventors call this statistical dental arch model Flexible Arch Model (FAM) and believe that FAM can be used to solve a lot of challenging problems in digital dentistry including automatic creation of a multi-unit restorative dental structure. In an exemplary embodiment, FAM is computed to capture and parameterize the variations of the multiple real dental arches in a training set. To perform this, the well-known PCA statistical method is used in an exemplary embodiment, though other statistical models such as k-means clustering could be used.

In the exemplary embodiment, the overall procedure to build the FAM includes the steps of acquiring multiple sets of digitized dental arches with a pair of maxillary (upper) and mandibular (lower) jaws in the right relative position (correct anatomical relationship). The multiple sets of digitized dental arches may be obtained by scanning upper and lower source dental arches separately and computing a correct bite registration of individual upper and lower arch scans, where the multiple sets of digitized dental arches include a set of complete 3D geometry of individual tooth models. The next step includes gathering a pre-defined set of landmark points on the occlusal surface of each arch all in the same order and same corresponding positions across multiple samples, using a manual process. For example, with N pairs of upper and lower arches in a training set, for the $i^{th}$ pair of arches the inventors define a vector of M landmark points as follows:

$$V^i = (P^1_x, P^1_y, P^1_z, P^2_x, P^2_y, P^2_z, \ldots, P^M_x, P^M_y, P^M_z).$$

In an exemplary embodiment, the landmark points include at least 4 points on the occlusal surface of individual posterior teeth, 2 points on an incisal edge, and 2 points on a cingulum area of anterior teeth. The gathered vectors of landmark points $(V^1, V^2, \ldots, V^N)$ are used to perform Principal Component Analysis in an exemplary embodiment to create a linear subspace of the feature points with the basis of principal components (or eigenvectors) found during the PCA procedure. With the computed statistical model, an arbitrary set of landmark points on a pair of upper and lower arches can be reconstructed by a linear combination of the statistical modeling coefficients (such as in PCA) to create a linear subspace of arch feature points within a reasonable range of variations captured from the training samples. The reconstructed landmark points can be used to build a full arch tooth model with individual crown models fit to a given set of arch points.

In an exemplary embodiment, using the feature points to construct the full arch tooth model with individual crown models comprises using the feature points to find a similarity transform from corresponding feature points on an anatomical crown model (ACM), using the found similarity transform to align each ACM to reconstructed arch points of the full arch tooth model initially, and for each ACM having adjacent teeth on both sides, measuring an amount of gap or overlap and computing an optimal new position for the tooth and scaling the tooth in a way that minimizes an amount of gap or overlap on both sides of the tooth. The similarity transform may be obtained by using a Procrustes analysis between two corresponding point sets.

Further exemplary embodiments include fitting the constructed full arch tooth model to an arbitrary arch scan of a patient's mouth by calculating a set of parameters for the full arch tooth model that minimizes a penalty function between a target arch of the arbitrary arch scan and each respective parameter by building a full arch tooth model using initial parameters, computing the penalty function between the target arch and the respective parameter, modifying the respective parameter to reduce the penalty function, iterating to find a lowest penalty function, and using the respective parameters to update the full arch tooth model. By way of example, the parameters may include statistical modeling coefficients of the full arch tooth model and rigid transformation data. In an exemplary embodiment, the penalty function is computed as:

$$E(\theta, \alpha) = \Sigma_{i=1}^N \|F_i(\theta, \alpha) - S_i(\theta, \alpha)\|^2$$

where $E(\theta, \alpha)$ is minimized in terms of transformation parameters ($\theta$) and statistical parameters of the full arch tooth model ($\alpha$) to be found, where $F_i(\theta, \alpha)$ is a point on the surface of the full arch tooth model at given optimization parameters and $S_i(\theta, \alpha)$ is a corresponding point on a surface of a target arch scan. Missing teeth on the target arch scan may be accounted for by aligning an average full arch tooth model to the target arch by a rough estimation and classifying a tooth on the target arch scan as "missing" if a closest point from a tooth in the full arch tooth model to the target arch scan is greater than a pre-determined threshold value.

The invention further includes a system having a processor and instructions stored in a memory that when executed by the processor implement the methods described herein. These and other embodiments will become apparent to those skilled in the art from the following detailed description of the invention.

BRIEF DESCRIPTION OF THE DRAWINGS

Exemplary embodiments of the invention will be described in conjunction with the associated figures.

DETAILED DESCRIPTION OF ILLUSTRATIVE EMBODIMENTS

Figure 1:
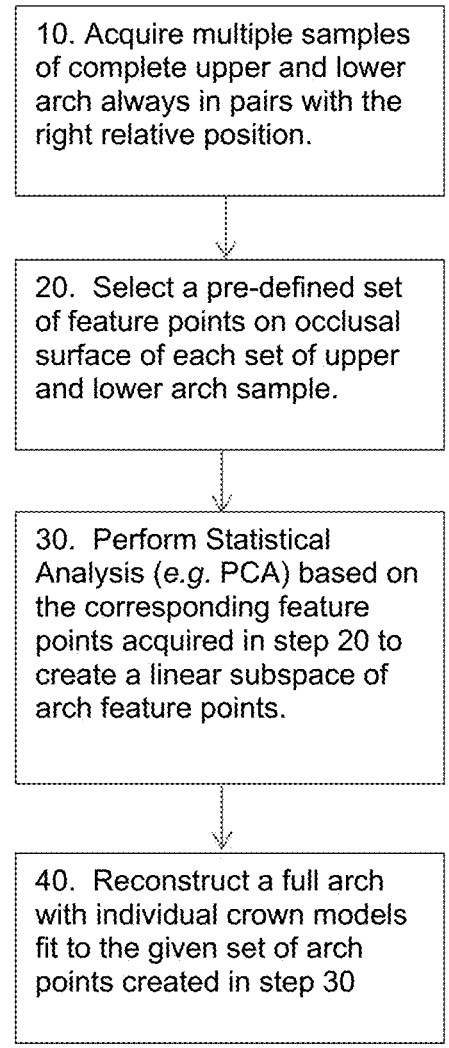
FIG. 1 illustrates the process of building a flexible arch model in accordance with an embodiment of the invention.

Certain specific details are set forth in the following description with respect to FIGS. 1-5 to provide a thorough understanding of various embodiments of the invention. Certain well-known details are not set forth in the following disclosure, however, to avoid unnecessarily obscuring the various embodiments of the invention. Those of ordinary skill in the relevant art will understand that they can practice other embodiments of the invention without one or more of the details described below. Also, while various methods are described with reference to steps and sequences in the following disclosure, the description is intended to provide a clear implementation of embodiments of the invention, and the steps and sequences of steps should not be taken as required to practice the invention.

By way of overview, the Flexible Arch Model (FAM) developed by the inventors is computed to capture and parameterize the variations of the multiple real dental arches in a training set. To perform this, the inventors use a well-known statistical method called Principal Component Analysis (PCA) in an exemplary embodiment. As known to those skilled in the art, PCA has been used to generate a statistical tooth model and to produce denture parts or tooth restorations using electronic dental representations as described in U.S. Pat. No. 8,727,776 to Mehl. PCA reduces the complexity of modeling an anatomical shape by looking at the characteristics of a set of samples and defining those elements of the sample that best characterize differences across the samples. A similar approach is described by Gurke in "Generating geometrically deformable models by statistical shape modeling for computer aided dental restorations," CARS 2000, Lemke, et al. editors (2000), which describes development of a tooth model based on a form of statistical shape analysis known as the Point Distribution Model including an analysis of the shape variance of a training set using eigenvectors and the definition of significant dental medical features. The weighted amounts of each eigenvector are added to the mean tooth shape of the training set to define the tooth model. The tooth model is used in an automatic CAD system for dental restorations. C. Lorenz, et al. also described in an article entitled "Generation of point based 3D statistical shape models for anatomical objects," Computer Vision and Image Understanding, Vol. 77, Issue 2, pages 175-191, February 2000, a technique for the generation of a statistical shape model for medical objects using PCA where a template shape is developed and all objects to be analyzed are fitted to the template. The disclosures of these documents is hereby incorporated by reference to explain to those skilled in the art how to implement PCA in the context of restorative dentistry as described herein. Furthermore, those skilled in the art will appreciate that PCA is not the only statistical modeling approach that can be used to generate an adequate dental arch model for use with the FAM method and other statistical models (e.g., k-means clustering) may be readily substituted for PCA herein.

The overall procedure to build the FAM is described below and summarized in the flow diagram in FIG. 1. Those skilled in the art will appreciate that the flow diagram of FIG. 1 is implemented in software loaded onto a computer processor in an exemplary embodiment. In particular, the instructions comprising the computer software are stored in a memory element and loaded into a computer processor that executes the instructions to implement the method exemplified by the flow diagram of FIG. 1. In exemplary embodiments, the computer processor is in operative communication with an instruction memory (both not shown) with instructions for implementing an operating system and application programs for implementing the techniques for creating a full arch model as described with respect to FIG. 1. The processor may include a standardized processor, a specialized processor, a microprocessor, or the like. The processor executes instructions including, for example, instructions for implementing the techniques described in more detail below. The instruction memory stores the instructions that may be executed by the processor and may include computer readable storage media in the form of volatile and/or nonvolatile memory such as random access memory (RAM), read only memory (ROM), cache, Flash memory, a hard disk, or any other suitable storage component. As described herein, a computer readable storage media does not include a modulated data signal. In one embodiment, the instruction memory may be a separate component in communication with the processor, while in another embodiment, the instruction memory may be integrated into the processor.

As shown in FIG. 1, the first step in building the FAM is to acquire at step 10 multiple sets of digitized dental arches with a pair of maxillary (upper) and mandibular (lower) jaws in the right relative position (correct anatomical relationship). Often, this process requires multiple scanning of the source dental arches. For example, to acquire the full occlusal surface of each arch, the upper and lower arches would need to be scanned separately, and additional scanning of the combined upper and lower arches should be used to compute the correct bite registration of the individual upper and lower arch scans. Of course, the relative position and the number of scans may be varied so long as full, consistent data sets of the dental arches are obtained.

Then, at step 20, a pre-defined set of landmark points on the occlusal surface of each arch is gathered in the same order and same corresponding positions across multiple samples, typically using a manual process. For example, with N pairs of upper and lower arches in a training set, the $i^{th}$ pair of arches a vector of M landmark points is defined as:

$$V^i = (P^1_x, P^1_y, P^1_z, P^2_x, P^2_y, P^2_z, \ldots, P^M_x, P^M_y, P^M_z).$$

The vectors of landmark points $(V^1, V^2, \ldots, V^N)$ gathered in step 20 are then used at step 30 to perform Principal Component Analysis (or k-means clustering or other form of statistical analysis) in an exemplary embodiment to create a linear subspace of the feature points with the basis of principal components (or eigenvectors) found during the PCA procedure. With the statistical model computed in step 30, an arbitrary set of landmark points on a pair of upper and lower arches are reconstructed at step 40 by a linear combination of the principal components (when PCA is used as the statistical model) within a reasonable range of variations captured from the training samples. The reconstructed landmark points are used to build a full set of tooth models in a dental arch. This method of reconstructing the full geometry of a dental arch will be described in more detail below.

Figure 2:
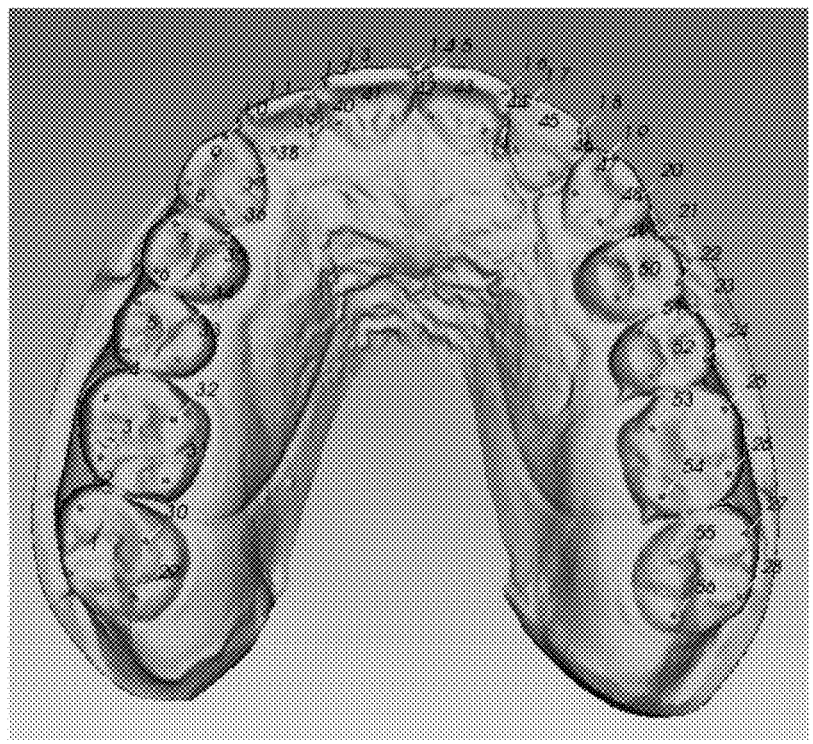
FIG. 2 illustrates typical feature point selection for an upper arch scan.
Figure 3:
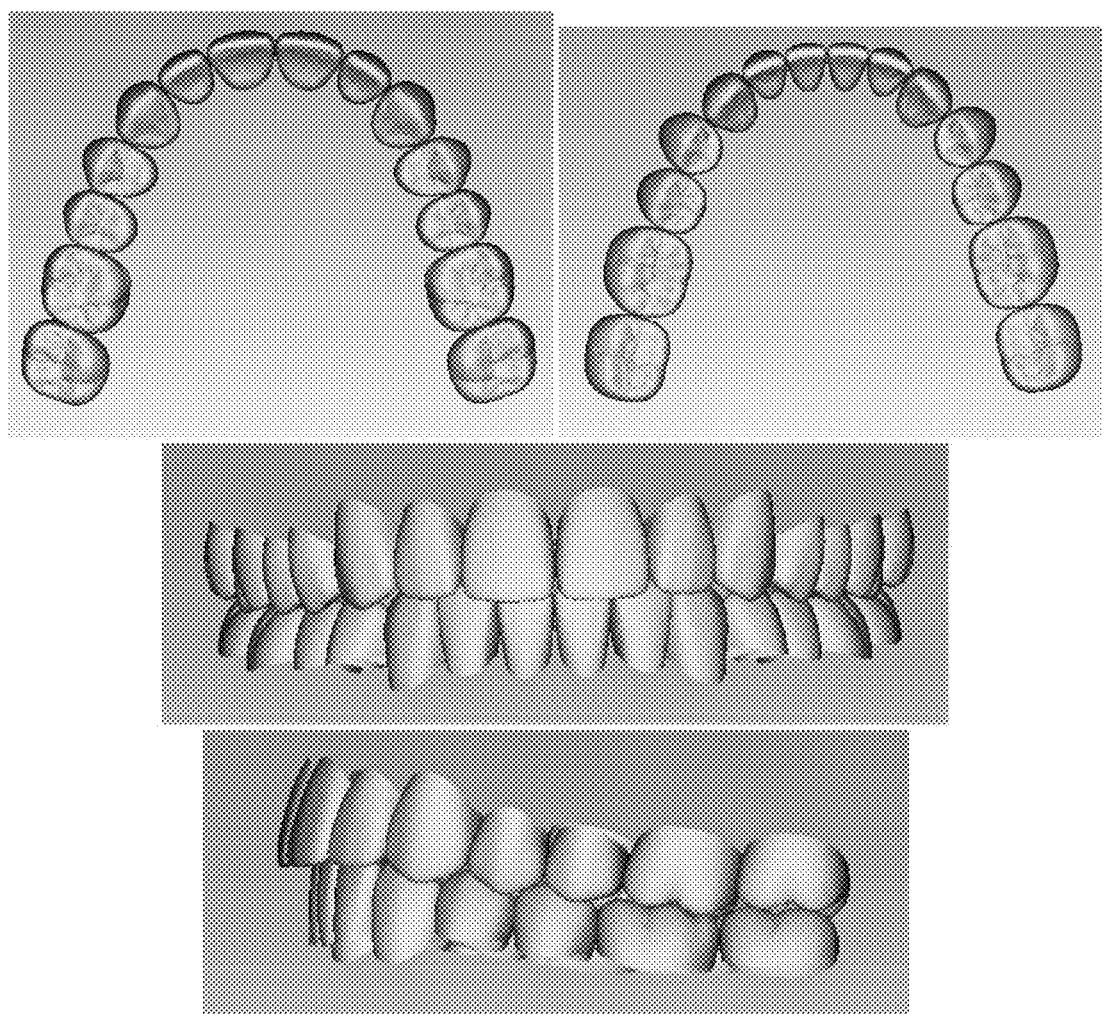
FIG. 3 illustrates the average FAM from different angles: (top left) upper jaw, (top right) lower jaw, (middle) full arch from a front view, (bottom) full arch from a side view and shows the results of applying the steps of aligning individual average crown models to the average set of arch points.

The FAM so constructed includes two parts. The first part includes principal components (when PCA is used as the statistical model) of a set of feature points that represents important features of each tooth in a full dental arch per arch type (upper or lower). Each sample of the training set of the statistical model (e.g., PCA) is a set of feature points and not the entire point cloud of the arch. FIG. 2 shows a typical set of feature points (1-56) selected from an upper arch scan. The main purpose of this step is to capture variations and constraints in the overall shape of the arch (not detailed individual shape of teeth) and relative positioning among teeth in the arch. The full geometry of an arbitrary dental arch can be constructed by the computational counterpart of FAM using the second part of FAM, which is a fast computational model that provides an alignment of individual ACMs to the given set of feature points generated by the first part of FAM.

Part 1 of FAM is rather straightforward and it can be computed by a mathematical procedure for statistical modeling, for example, the procedure called PCA noted above, once the full set of manually picked individual feature points across many full dental arches (e.g. 100) is obtained. At least 4 points on the occlusal surface of individual posterior teeth, 2 points on the incisal edge and 2 points on the cingulum area of anterior teeth should be collected to make the algorithm work with sufficient particularity as described in Part 2.

Part 2 of FAM is more challenging to establish. Given a set of feature points reconstructed in Part 1, a full set of individual crown models (ACM) are aligned that approximate the given set of feature points in the arch and also look natural with proper relationship between adjacent units by a very fast computational operation. This operation needs to be performed fast enough so that it could be used as an iterative operational unit to solve a bigger numerical optimization problem. An algorithm has been developed to meet the requirements of part 2 of FAM and includes the following steps.

First, the 4 (or more) points on the occlusal surface (incisal/lingual surface for anterior) of an individual tooth in the arch are used to find a similarity transform from the corresponding feature points on the ACM. A Procrustes analysis is used to find such a similarity transform (rigid transform+uniform scaling) between two corresponding point sets. As known to those skilled in the art, a Procrustes analysis is a form of statistical shape analysis used to analyze the distribution of a set of shapes by optimally superimposing the shapes until they have similar placement and size and then minimizing a measure of shape difference called the Procrustes distance between the shapes.

Second, the similarity transform found between each tooth in the arch and ACM is used to align each ACM to the reconstructed arch points initially, which may leave a space or overlap between two adjacent ACMs after the alignment.

Third, for each of the non-boundary teeth (i.e. teeth with adjacent teeth on both sides), measure the amount of gap or overlap, and compute its optimal new position and scale in a way that minimizes the amount of gap or overlap on both sides.

The FAM so constructed (FIG. 3) allows one, given a set of a small number of (e.g. ~5-15) statistical modeling coefficients (such as in PCA), to reconstruct any arbitrary shape of a full (upper or lower) arch that consists of average ACMs with enough constraints that would make the entire arch look natural. The reconstruction step is performed very fast and may be used as a part of a bigger numerical optimization problem.

Figure 4:
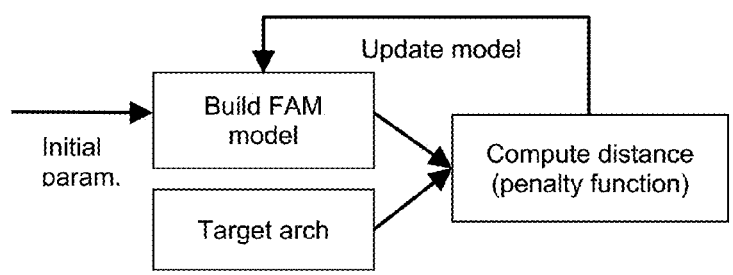
FIG. 4 illustrates an optimization framework to fit FAM to a given (scanned) arch.

To be able to use the arch model as so constructed for various dental applications such as automatic dental feature detection and crown initialization, it is important to be able to fit the FAM to a real arch scan of a patient's mouth. This process is performed with an optimization framework where a set of parameters of FAM that minimizes the distance between FAM and a given scanned arch is found as illustrated in FIG. 4. In FIG. 4, the process includes building FAM model based on initial parameters, computing the distance (penalty function) between the target arch and the FAM parameter, modifying the FAM parameters to reduce the penalty function, and iterating the loop to find the lowest penalty function (best fit). The optimization parameters include statistical modeling coefficients of FAM and rigid transformation (rotation and translation) data. The FAM reconstructed by the optimization parameters and the stored target arch data are compared to compute a distance between corresponding feature points and the optimization parameters so determined are fed back to the FAM to update the model.

The optimization process of FIG. 4 is structured as a non-linear least square problem and is solved by a numerical method called Levenberg-Marquardt algorithm. Eq. 1 is the cost (penalty) function that is to be minimized in terms of the transformation parameters ($\theta$) and the statistical parameters of the arch model ($\alpha$) to be found, where $F_i(\theta, \alpha)$ is a point on the surface of FAM at the given optimization parameters and $S_i(\theta, \alpha)$ is a corresponding point on the surface of the target arch scan.

$$E(\theta,\alpha)=\Sigma_{i=1}^{N}\|F(\theta,\alpha)-S_i(\theta,\alpha)\|^2 \qquad \text{Eq. 1}$$

One of the main challenges in computing the cost function (Eq. 1) is to find the corresponding N surface points between FAM and the target arch scan automatically. One has complete knowledge on the feature points of FAM (e.g. the location of a cusp point of tooth #5). On the other hand, one does not have any prior knowledge on the corresponding feature points on the target arch. Sometimes, there will be no corresponding surface points between FAM and the arch scan on certain teeth due to the missing teeth and/or partial scanning of the arch. To deal with the lack of knowledge on the feature points of the target arch scan, a similar approach to Iterative Closest Point (ICP) algorithm is used. In the ICP algorithm, the correspondence between the two sets of point clouds is established on the fly by finding the closest point to the target set from any point of the reference set at each iteration. Additionally, to take missing teeth on the arch scan into account, the average FAM is aligned to the target arch by a rough estimation and a tooth on the arch scan is classified as "missing" if the closest point from the tooth in FAM to the arch scan is greater than a pre-determined threshold value. The surface points of FAM on the classified "missing" tooth would not be included in the computation of the cost function (Eq. 1).

A step that does not have an obvious solution in the optimization framework described herein is the initial estimation of the optimization parameters. Especially, the pre-alignment step (i.e. estimating the transformation parameters) is important for the subsequent iterative process to converge to the optimal solution. To be able to align two arch models correctly along the occlusal axis of the arch, at least two corresponding 3D feature points are desired. This minimal set of corresponding feature points could be found either manually or automatically utilizing some 3D feature detection algorithms. For the implementation described herein, the inventors use implant locations that are detected automatically during the arch scan process and use a subsequent in-house dental feature detection algorithm to identify this minimal set of feature correspondence. However, the proposed fitting method still can be developed with other feature detection algorithms or even by establishing the minimum set of correspondence in a manual manner.

Figure 5:
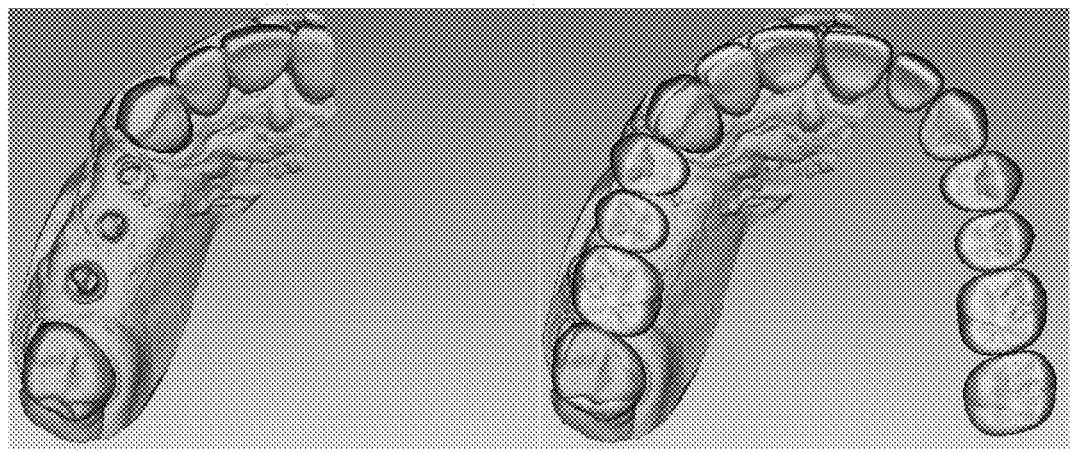
FIG. 5 illustrates the result of FAM fitting to a partial arch scan (upper jaw).

FIG. 5 shows the results of the optimization process for a partial arch scan with a space for three missing teeth, which demonstrates the ability of the fitting algorithm that works with only a small portion of a full arch scan and extrapolates the rest of the arch based on the available fitting area. This fitting algorithm generally finds an optimal set of arch parameters and transform parameters that provide the closest match to the target arch scan.

By way of summary, to implement the above method, an existing anatomical (statistical) crown model (based on k-means clustering or other statistical model known to those skilled in the art) is used with a new statistical arch model including average and statistical modeling (e.g., PCA) components of landmark points of many real arch scans and a computational model that aligns average crown models to a set of arch feature points. A fitting method is also used to fit the arch model to an arbitrary real arch scan. The resulting modified FAM is then optimized to fit to the real arch scan of the patient's mouth to create a customized arch for the patient.

Those skilled in the art will appreciate that the methods and models described herein may be used for dental feature detection, crown initialization, and automated design of arches. The approach described herein adds value to digital dentistry by advancing techniques for automated processing of patient specific dentition environment. Those skilled in the art will further appreciate that the methods described herein address errors caused by how the upper and lower jaw come together and reduces the amount of scan data needed by using an underlying statistical model framework for the scan data. The novel processing steps described herein thus improve the functioning of the computer by speeding up the processing for arch model creation while increasing the accuracy of the resulting arch model.

Those skilled in the art will appreciate that the techniques described herein add value to dentistry by enabling the creation of a customized arch for patients. Those skilled in the art also will readily appreciate that many additional modifications and scenarios are possible in the exemplary embodiments without materially departing from the novel teachings and advantages of the invention. Accordingly, any such modifications are intended to be included within the scope of this invention as defined by the following exemplary claims.

What is claimed:

1. A method for creating a full arch model comprising an upper and lower jaw in a correct anatomical relationship using a statistical technique applied to a set of individual tooth models, comprising the steps of:
   acquiring multiple sets of digitized dental arches with a pair of maxillary upper and mandibular lower jaws in a correct anatomical relationship;
   gathering a pre-defined set of landmark points on the occlusal surface of each arch all in the same order and same corresponding positions across multiple arches;
   using the gathered set of landmark points to perform statistical modeling to create a linear subspace of arch feature points; and
   using the feature points to construct a full arch tooth model with individual crown models fit to a given set of arch points.

2. The method of claim 1, wherein acquiring the multiple sets of digitized dental arches comprises scanning upper and lower source dental arches separately and computing a correct bite registration of individual upper and lower arch scans.

3. The method of claim 2, wherein the multiple sets of digitized dental arches include a set of complete 3D geometry of individual tooth models.

4. The method of claim 1, wherein gathering the pre-defined set of landmark points comprises with N pairs of upper and lower arches in a training set, defining for an $i^{th}$ pair of arches a vector of M landmark points as follows:

$$V^i = (P^1_x, P^1_y, P^1_z, P^2_x, P^2_y, P^2_z, \ldots, P^M_x, P^M_y, P^M_z).$$

5. The method of claim 4, wherein the landmark points comprise at least 4 points on the occlusal surface of individual posterior teeth, 2 points on an incisal edge, and 2 points on a cingulum area of anterior teeth.

6. The method of claim 1, wherein the statistical modeling is performed using Principal Component Analysis (PCA) to create a linear subspace of the feature points with the basis of principal components or eigenvectors found during a PCA procedure.

7. The method of claim 1, wherein using the feature points to construct the full arch tooth model with individual crown models comprises the steps of using the feature points to find a similarity transform from corresponding feature points on an anatomical crown model (ACM), using the found similarity transform to align each ACM to reconstructed arch points of the full arch tooth model initially, and for each ACM having adjacent teeth on both sides, measuring an amount of gap or overlap and computing an optimal new position for a tooth and scaling the tooth in a way that minimizes an amount of gap or overlap on both sides of the tooth.

8. The method of claim 7, wherein the similarity transform is obtained by using a Procrustes analysis between two corresponding point sets.

9. The method of claim 1, further comprising fitting the constructed full arch tooth model to an arbitrary arch scan of a patient's mouth.

10. The method of claim 9, wherein a set of parameters is calculated for the full arch tooth model that minimizes a penalty function between a target arch of the arbitrary arch scan and each respective parameter by building a full arch tooth model using initial parameters, computing the penalty function between the target arch and the respective parameter, modifying the respective parameter to reduce the penalty function, iterating to find a lowest penalty function, and using the respective parameters to update the full arch tooth model.

11. The method of claim 10, wherein the parameters include statistical modeling coefficients of the full arch tooth model and rigid transformation data.

12. The method of claim 11, wherein the penalty function is:

$$E(\theta, \alpha) = \Sigma_{i=1}^{N} \|F_i(\theta, \alpha) - S_i(\theta, \alpha)\|^2$$

where $E(\theta, \alpha)$ is minimized in terms of transformation parameters ($\theta$) and statistical parameters of the full arch tooth model ($\alpha$) to be found, where $F_i(\theta, \alpha)$ is a point on the surface of the full arch tooth model at given optimization parameters and $S_i(\theta, \alpha)$ is a corresponding point on a surface of a target arch scan.

13. The method of claim 12, wherein missing teeth on the target arch scan are accounted for by aligning an average full arch tooth model to the target arch by a rough estimation and classifying a tooth on the target arch scan as "missing" if a closest point from a tooth in the full arch tooth model to the target arch scan is greater than a pre-determined threshold value.

14. A system that creates a full arch model comprising an upper and lower jaw in a correct anatomical relationship using a statistical technique applied to a set of individual tooth models, comprising:
   a processor; and
   a memory that includes instructions for execution by the processor, said instructions when executed causing said processor to implement a method including the steps of:
   acquiring multiple sets of digitized dental arches with a pair of maxillary (upper and mandibular lower jaws in a correct anatomical relationship,
   gathering a pre-defined set of landmark points on the occlusal surface of each arch all in the same order and same corresponding positions across multiple arches,
   using the gathered set of landmark points to perform statistical modeling to create a linear subspace of arch feature points, and
   using the feature points to construct a full arch tooth model with individual crown models fit to a given set of arch points.

15. The system of claim 14, wherein the memory further includes instructions that when executed by the processor implement the additional step of scanning upper and lower source dental arches separately and computing a correct bite registration of individual upper and lower arch scans, where the multiple sets of digitized dental arches include a set of complete 3D geometry of individual tooth models.

16. The system of claim 14, wherein the memory further includes instructions that when executed by the processor implements the step of gathering the pre-defined set of landmark points from N pairs of upper and lower arches in a training set, by defining for an $i^{th}$ pair of arches a vector of M landmark points as follows:

$$V^i = (P^1_x, P^1_y, P^1_z, P^2_x, P^2_y, P^2_z, \ldots, P^M_x, P^M_y, P^M_z).$$

where the landmark points comprise at least 4 points on the occlusal surface of individual posterior teeth, 2 points on an incisal edge, and 2 points on a cingulum area of anterior teeth.

17. The system of claim 14, wherein the statistical modeling is performed using Principal Component Analysis (PCA) software that creates a linear subspace of the feature points with the basis of principal components or eigenvectors found during a PCA procedure.

18. The system of claim 14, wherein the memory further includes instructions that when executed by the processor implements the step of using the feature points to construct the full arch tooth model with individual crown models by executing instructions for implementing the steps of using the feature points to find a similarity transform from corresponding feature points on an anatomical crown model (ACM), using the found similarity transform to align each ACM to reconstructed arch points of the full arch tooth model initially, and for each ACM having adjacent teeth on both sides, measuring an amount of gap or overlap and computing an optimal new position for a tooth and scaling the tooth in a way that minimizes an amount of gap or overlap on both sides of the tooth.

19. The system of claim 14, wherein the memory further includes instructions that when executed by the processor implements the further step of fitting the constructed full arch tooth model to an arbitrary arch scan of a patient's mouth, wherein a set of parameters is calculated for the full arch tooth model that minimizes a penalty function between a target arch of the arbitrary arch scan and each respective parameter by building a full arch tooth model using initial parameters, computing the penalty function between the target arch and the respective parameter, modifying the respective parameter to reduce the penalty function, iterating to find a lowest penalty function, and using the respective parameters to update the full arch tooth model.

20. The system of claim 19, wherein the parameters include statistical modeling coefficients of the full arch tooth model and rigid transformation data and wherein the penalty function is:

$$E(\theta,\alpha)=\Sigma_{i=1}^{N}\|F_i(\theta,\alpha)-S_i(\theta,\alpha)\|^2$$

where $E(\theta, \alpha)$ is minimized in terms of transformation parameters ($\theta$) and statistical parameters of the full arch tooth model ($\alpha$) to be found, where $F_i(\theta, \alpha)$ is a point on the surface of the full arch tooth model at given optimization parameters and $S_i(\theta, \alpha)$ is a corresponding point on a surface of a target arch scan.

* * * * *